United States Patent
Shalyaev et al.

(10) Patent No.: US 6,365,538 B1
(45) Date of Patent: *Apr. 2, 2002

(54) METHOD AND CATALYST SYSTEM FOR PRODUCING AROMATIC CARBONATES

(75) Inventors: Kirill Vladimirovich Shalyaev, Clifton Park; Grigorii Lev Soloveichik, Latham; Bruce Fletcher Johnson, Scotia; Donald Wayne Whisenhunt, Jr., Niskayuna, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/495,538

(22) Filed: Jan. 31, 2000

(51) Int. Cl.$^7$ ............... B01J 31/00; B01J 27/06; B01J 27/128; B01J 23/58; B01J 23/40

(52) U.S. Cl. .......... 502/159; 502/172; 502/224; 502/229; 502/230; 502/302; 502/304; 502/326; 502/328; 502/330; 502/339; 502/349; 502/350; 502/353

(58) Field of Search .................... 502/159, 172, 502/224, 229, 230, 302, 304, 326, 328, 330, 339, 349, 350, 353

(56) References Cited

U.S. PATENT DOCUMENTS

| | | | |
|---|---|---|---|
| 4,187,242 A | 2/1980 | Chalk | 260/463 |
| 4,859,644 A | * 8/1989 | Van Broekhoven et al. | 502/154 |
| 5,231,210 A | 7/1993 | Joyce et al. | 558/274 |

(List continued on next page.)

FOREIGN PATENT DOCUMENTS

| | | |
|---|---|---|
| DE | EP736325 | 3/1996 |
| EP | 0 350 700 | 1/1990 |
| JP | 10158221 | 6/1980 |
| JP | 94-271506 | 9/1994 |
| JP | 94-271509 | 9/1994 |
| JP | 95-145107 | 6/1995 |
| JP | 96-89810 | 4/1996 |
| JP | 96-92168 | 4/1996 |
| JP | 96-193056 | 7/1996 |
| JP | 97-110804 | 4/1997 |
| JP | 97-255629 | 9/1997 |
| JP | 97-27815 | 10/1997 |
| JP | 97-278716 | 10/1997 |

OTHER PUBLICATIONS

European Search Report for International Application No. PCT/US 00/28716.

Primary Examiner—Mark L. Bell
Assistant Examiner—Patricia L. Hailey
(74) Attorney, Agent, or Firm—Ben P. Patel; Donald S. Ingraham

(57) ABSTRACT

A method and catalyst system for producing aromatic carbonates from aromatic hydroxy compounds. In one embodiment, the method includes the step of contacting at least one aromatic hydroxy compound with oxygen and carbon monoxide in the presence of a carbonylation catalyst system having catalytic amounts of the following components: a Group VIII B metal source; an alkaline metal chloride; a polyether; and a base. Alternative embodiments substitute a catalytic amount of a nitrile promoter for the polyether.

13 Claims, 1 Drawing Sheet

U.S. PATENT DOCUMENTS

| | | | |
|---|---|---|---|
| 5,239,106 A | 8/1993 | Shafer | 558/274 |
| 5,284,964 A | 2/1994 | Pressman et al. | 558/260 |
| 5,373,083 A | 12/1994 | King et al. | 528/199 |
| 5,380,907 A | 1/1995 | Mizukami et al. | 558/270 |
| 5,399,734 A | 3/1995 | King et al. | 558/270 |
| 5,498,789 A | 3/1996 | Takagi et al. | 558/270 |
| 5,502,232 A | 3/1996 | Buysch et al. | 558/270 |
| 5,543,547 A | 8/1996 | Iwane et al. | 558/274 |
| 5,726,340 A | 3/1998 | Takagi et al. | 558/274 |
| 5,760,272 A | 6/1998 | Pressman et al. | 558/274 |
| 5,767,303 A | 6/1998 | Minami et al. | 558/275 |
| 5,821,377 A | 10/1998 | Buysch et al. | 558/274 |
| 5,856,554 A | 1/1999 | Buysch et al. | 558/274 |
| 6,001,768 A * | 12/1999 | Buysch et al. | 502/230 |
| 6,114,563 A * | 9/2000 | Spivack et al. | 558/274 |
| 6,172,254 B1 * | 1/2001 | Pressman et al. | 558/274 |

* cited by examiner

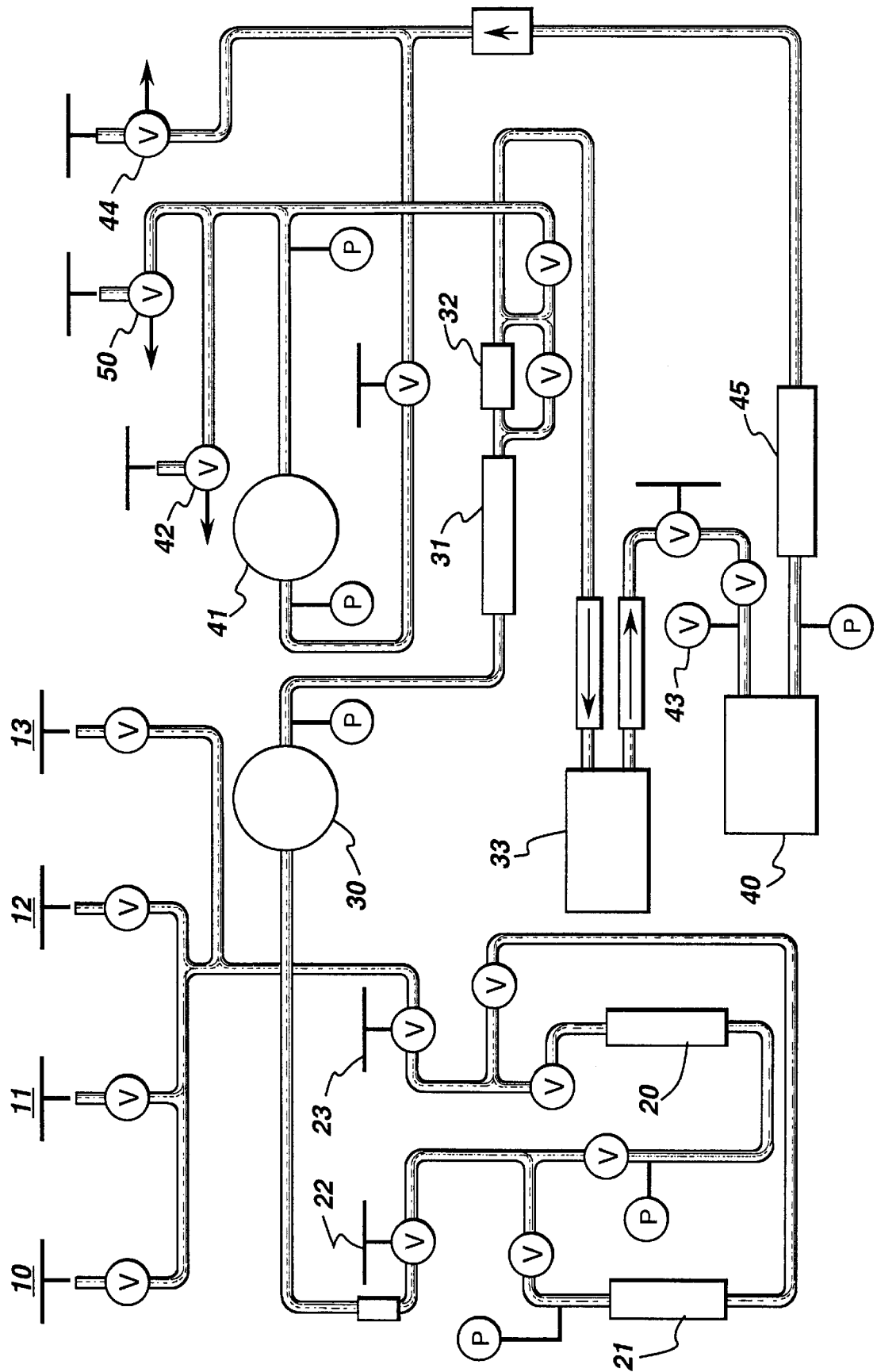

METHOD AND CATALYST SYSTEM FOR PRODUCING AROMATIC CARBONATES

BACKGROUND

1. Field of the Invention

The present invention is directed to a method and catalyst system for producing aromatic carbonates and, more specifically, to a method and catalyst system for producing diaryl carbonates through the carbonylation of aromatic hydroxy compounds.

2. Discussion of Related Art

Aromatic carbonates find utility, inter alia, as intermediates in the preparation of polycarbonates. For example, a popular method of polycarbonate preparation is the melt transesterification of aromatic carbonates with bisphenols. This method has been shown to be environmentally superior to previously used methods which employed phosgene, a toxic gas, as a reagent and chlorinated aliphatic hydrocarbons, such as methylene chloride, as solvents.

Various methods for preparing aromatic carbonates have been previously described in the literature and/or utilized by industry. A method that has enjoyed substantial popularity in the literature involves the direct carbonylation of aromatic hydroxy compounds with carbon monoxide and oxygen. In general, practitioners have found that the carbonylation reaction requires a rather complex catalyst system. For example, in U.S. Pat. No. 4,187,242, which is assigned to the assignee of the present invention, Chalk reports that a carbonylation catalyst system should contain a Group VIII B metal, such as ruthenium, rhodium, palladium, osmium, iridium, platinum, or a complex thereof. Further refinements to the carbonylation reaction include the identification of organic co-catalysts, such as terpyridines, phenanthrolines, quinolines and isoquinolines in U.S. Pat. No. 5,284,964 and the use of certain halide compounds, such as quaternary ammonium or phosphonium halides in U.S. Pat. No. 5,399,734, both patents also being assigned to the assignee of the present invention.

The economics of the carbonylation process is strongly dependent on the number of moles of aromatic carbonate produced per mole of Group VIII B metal utilized (i.e. "catalyst turnover"). Consequently, much work has been directed to the identification of efficacious catalyst combinations that increase catalyst turnover. In U.S. Pat. No. 5,231,210, which is also assigned to the present assignee, Joyce et al. report the use of a cobalt pentadentate complex as an inorganic co-catalyst ("IOCC"). In U.S. Pat. No. 5,498,789, Takagi et al. report the use of lead as an IOCC. In U.S. Pat. No. 5,543,547, Iwane et al. report the use of trivalent cerium as an IOCC. In U.S. Pat. No. 5,726,340, Takagi et al. report the use of lead and cobalt as a binary IOCC system.

Carbonylation catalyst literature lauds the effectiveness of onium halide compounds, bromides in particular, as a halide source in the catalyst system. For example, in GB 2311777, Takagi et al. state the traditional understanding that onium bromide sources are the preferred halide sources for carbonylation catalyst systems. While it is true that onium halide compounds have historically exhibited high activity, there are drawbacks to using onium halides generally, and bromides in particular, in the carbonylation reaction. Initially, it is worth noting that, when used to carbonylate phenol, bromide ion is consumed in the process—forming undesirable brominated byproducts, such as 2- and 4-bromophenols and bromo diphenylcarbonate. These byproducts must typically be recovered and recycled, further adding to the investment and operating cost of the process. Furthermore, onium halides are significantly more expensive than alkali metal halides. However, due to their comparatively low activity, the alkali metal halides have not traditionally been considered an economically viable alternative to onium bromides.

Unfortunately, the literature is not instructive regarding the role of many catalyst components in the carbonylation reaction (i.e. the reaction mechanism). Accordingly, meaningful guidance regarding the identification of effective combinations of catalyst system components is cursory at best. For example, periodic table groupings have failed to provide guidance in identifying additional IOCC's. Typical of this problem is U.S. Pat. No. 5,856,554, which provides a general listing of possible IOCC candidates. However, further analysis has revealed that a substantial number of the members (and combinations of members) of the recited groups (i.e., Groups IV B and V B) are not effective IOCC's. Therefore, due to the lack of guidance in the literature, the identification of effective carbonylation catalyst systems has become a serendipitous exercise.

As the demand for high performance plastics has continued to grow, new and improved methods of providing product more economically are needed to supply the market. In this context, various processes and catalyst systems are constantly being evaluated; however, the identities of improved and/or additional effective catalyst systems for these processes continue to elude the industry. Consequently, a long felt, yet unsatisfied need exists for new and improved methods and catalyst systems for producing aromatic carbonates and the like.

SUMMARY OF THE INVENTION

Accordingly, the present invention is directed to a method and catalyst system for producing aromatic carbonates. In one embodiment, the method includes the step of contacting at least one aromatic hydroxy compound with oxygen and carbon monoxide in the presence of a carbonylation catalyst system having catalytic amounts of the following components: a Group VIII B metal source; an alkaline metal chloride; a polyether; and a base.

Alternative embodiments substitute a catalytic amount of a nitrile promoter for the polyether. Further alternative embodiments of the carbonylation catalyst system can include catalytic amounts of at least one inorganic cocatalyst comprising a non-Group VIII B metal source, such as lead or combinations of copper and titanium; lead and cerium; lead and titanium; or copper and zirconium.

BRIEF DESCRIPTION OF THE DRAWING

Various features, aspects, and advantages of the present invention will become more apparent with reference to the following description, appended claims, and accompanying drawing, wherein the FIGURE is a schematic view of a device capable of performing an aspect of an embodiment of the present invention.

DETAILED DESCRIPTION OF PREFERRED EMBODIMENTS

The present invention is directed to a method and catalyst system for producing aromatic carbonates. In one embodiment, the method includes the step of contacting at least one aromatic hydroxy compound with oxygen and carbon monoxide in the presence of a carbonylation catalyst system having catalytic amounts of the following components: a Group VIII B metal source; an alkaline metal chloride; a polyether; and a base.

For convenience, the constituents of the catalyst system described herein are called "components" irrespective of whether a reaction between specific components actually occurs either before or during the carbonylation reaction.

Therefore, the catalyst system may include the components and any reaction products thereof.

Unless otherwise noted, the term "catalytic amount," as used herein, includes that amount of a component capable of either increasing (directly or indirectly) the yield of the carbonylation product or increasing selectivity toward an aromatic carbonate. Optimum amounts of a given component can vary based on reaction conditions and the identity of other components, yet can be readily determined in light of the discrete circumstances of a given application.

Aromatic hydroxy compounds which may be used in the present process include aromatic mono- or polyhydroxy compounds, such as phenol, cresol, xylenol, resorcinol, hydroquinone, and bisphenol A. Aromatic organic mono hydroxy compounds are preferred, with phenol being more preferred.

In various preferred embodiments, the carbonylation catalyst system contains at least one constituent from the Group VIII B metals or a compound thereof. A preferred Group VIII B constituent is a catalytic amount of a palladium source. The palladium source may be a non-supported Pd(II) salt or complex. As used herein, the term "non-supported" indicates the absence of industrially conventional catalyst supports based on carbon, element oxides, element carbides or element salts in various presentations. Examples of supports containing carbon are coke, graphite, carbon black and activated carbon. Examples of element oxide catalyst supports are $SiO_2$ (natural or synthetic silicas, quartz), $Al_2O_3$ ($\alpha$-, $\gamma$-$Al_2O_3$), aluminas, natural and synthetic aluminosilicates (zeolites), $TiO_2$ (rutile, anatase), $ZrO_2$ and $ZnO$. Examples of element carbides and salts are $SiC$, $AlPO_4$, $BaSO_4$, and $CaCO_3$.

Accordingly, suitable palladium sources include palladium halides, nitrates, carboxylates, oxides and palladium complexes containing carbon monoxide, amines, phosphines or olefins. As used herein, the term "complex" includes coordination or complex compounds containing a central ion or atom. The complexes may be nonionic, cationic, or anionic, depending on the charges carried by the central atom and the coordinated groups. Other common names for these complexes include complex ions (if electrically charged), Werner complexes, and coordination complexes.

In various applications, it may be preferable to utilize palladium(II) salts of organic acids, including carboxylates with $C_{2-6}$ aliphatic acids. Palladium(II) acetylacetonate and dichloro(1,4-bis(diphenylphosphino)butane) palladium(II) are also suitable palladium sources. Preferably, the amount of Group VIII B metal source employed should be sufficient to provide about 1 mole of metal per 800–10,000 moles of aromatic hydroxy compound. More preferably, the proportion of Group VIII B metal source employed should be sufficient to provide about 1 mole of metal per 2,000–5,000 moles of aromatic hydroxy compound.

The carbonylation catalyst system further contains a catalytic amount of an alkaline metal chloride. As used herein, the term "alkaline metal" includes the elements of Group I of the Periodic Table ("alkali metals") as well as the elements of Group II ("alkaline-earth metals"). Accordingly, a non-exclusive listing of preferred alkaline metal chlorides includes lithium chloride, sodium chloride, potassium chloride, and cesium chloride. In preferred embodiments, the carbonylation catalyst system can contain between about 5 and about 2000 moles of chloride per mole of palladium employed, and, more preferably, between about 50 and about 1000 molar equivalents of chloride are used.

The carbonylation catalyst system also includes a catalytic amount of a base. Any desired bases or mixtures thereof, whether organic or inorganic may be used. A non-exclusive listing of suitable inorganic bases include alkali metal hydroxides and carbonates; $C_2$–$C_{12}$ carboxylates or other salts of weak acids; and various alkali metal salts of aromatic hydroxy compounds, such as alkali metal phenolates. Hydrates of alkali metal phenolates may also be used. Examples of suitable organic bases include tertiary amines and the like. Preferably, the base used is an alkali metal salt incorporating an aromatic hydroxy compound, more preferably an alkali metal salt incorporating the aromatic hydroxy compound to be carbonylated to produce the aromatic carbonate. A nonexclusive listing of suitable bases includes sodium phenoxide and sodium hydroxide. In preferred embodiments, between about 5 and about 1000 molar equivalents of base are employed (relative to palladium), and, more preferably, between about 100 and about 700 molar equivalents of base are used.

The carbonylation catalyst system can include a catalytic amount of a polyether; i.e., a compound containing two or more C—O—C linkages. The polyether is preferably free from hydroxy groups to maximize its desired activity and avoid competition with the aromatic hydroxy compound in the carbonylation reaction. Preferred polyethers contain two or more C—O—C units. The polyether may be aliphatic or mixed aliphatic-aromatic. As used in the identification of the polyether, the term "aliphatic" refers to the structures of hydrocarbon groups within the molecule, not to the overall structure of the molecule. Thus, "aliphatic polyether" includes heterocyclic polyether molecules containing aliphatic groups within their molecular structure. Illustrative aliphatic polyethers include diethylene glycol dimethyl ether ("diglyme"); triethylene glycol dimethyl ether ("triglyme"); tetraethylene glycol dimethyl ether ("tetraglyme"); polyethylene glycol dimethyl ether; and crown ethers such as 15-crown-5 (1,4,7,10,13-pentaoxacyclopentadecane) and 18-crown-6 (1,4,7,10,13,16-hexaoxacyclooctadecane). Illustrative mixed aliphatic-aromatic polyethers include diethylene glycol diphenyl ether and benzo-18-crown-6.

In alternative embodiments, the polyether can be replaced with a catalytic amount of a nitrile promoter. Suitable nitrile promoters for the present method include $C_{2-8}$ aliphatic or $C_{7-10}$ aromatic mono- or dinitriles. Illustrative mononitriles include acetonitrile, propionitrile, and benzonitrile. Illustrative dinitriles include succinonitrile, adiponitrile, and benzodinitrile. Mononitriles are generally preferred; more specifically preferred is acetonitrile. It is noted that, contrary to the teachings of the prior art—some of which is identified supra, the function of the nitrile promoter in the present method is not simply that of an inert solvent. Rather, the nitrile is an active catalyst component that improves the yield of or selectivity toward the aromatic carbonate.

The carbonylation catalyst system can include catalytic amounts of one or more inorganic cocatalysts (IOCC's). It has been discovered that certain IOCC's and combinations of IOCC's effectively catalyze the carbonylation reaction in the presence of the aforementioned catalyst system components. Such IOCC's and combinations include lead; copper; lead and titanium; lead and cerium; lead and manganese; lead and zirconium; copper and titanium; copper and zirconium; copper and iron; copper and manganese; copper and nickel; copper and iron; and zinc and titanium. Additional IOCC's may be used in the carbonylation catalyst system, provided the additional IOCC does not deactivate (i.e. "poison") the original IOCC combination.

An IOCC can be introduced to the carbonylation reaction in various forms, including salts and complexes, such as tetradentate, pentadentate, hexadentate, or octadentate complexes. Illustrative forms may include oxides, halides, carboxylates, diketones (including beta-diketones), nitrates, complexes containing carbon monoxide or olefins, and the like. Suitable beta-diketones include those known in the art as ligands for the IOCC metals of the present system. Examples include, but are not limited to, acetylacetone, benzoylacetone, dibenzoylmethane, diisobutyrylmethane, 2,2-dimethylheptane-3,5-dione, 2,2,6-trimethylheptane-3,5-dione, dipivaloylmethane, and tetramethylheptanedione. The quantity of ligand is preferably not such that it interferes with the carbonylation reaction itself, with the isolation or purification of the product mixture, or with the recovery and reuse of catalyst components (such as palladium). An IOCC may be used in its elemental form if sufficient reactive surface area can be provided. However, it is preferable that an IOCC is non-supported as discussed above relative to the Group VII B metals.

IOCC's are included in the carbonylation catalyst system in catalytic amounts. In this context a "catalytic amount" is an amount of IOCC (or combination of IOCC's) that increases the number of moles of aromatic carbonate produced per mole of Group VIII B metal utilized; increases the number of moles of aromatic carbonate produced per mole of chloride utilized; or increases selectivity toward aromatic carbonate production beyond that obtained in the absence of the IOCC (or combination of IOCC's). Optimum amounts of an IOCC in a given application will depend on various factors, such as the identity of reactants and reaction conditions. For example, when palladium is included in the reaction, the molar ratio of copper relative to palladium at the initiation of the reaction is preferably between about 0.1 and about 100.

The carbonylation reaction can be carried out in a batch reactor or a continuous reactor system. Due in part to the low solubility of carbon monoxide in organic hydroxy compounds, such as phenol, it is preferable that the reactor vessel be pressurized. In preferred embodiments, gas can be supplied to the reactor vessel in proportions of between about 2 and about 50 mole percent oxygen, with the balance being carbon monoxide and, in any event, outside the explosion range for safety reasons. It is contemplated that oxygen can be supplied in diatomic form or from another oxygen containing source, such as peroxides and the like. Additional gases may be present in amounts that do not deleteriously affect the carbonylation reaction. The gases may be introduced separately or as a mixture. A total pressure in the range of between about 10 and about 250 atmospheres is preferred. Drying agents, typically molecular sieves, may be present in the reaction vessel. Reaction temperatures in the range of between about 60° C. and about 150° C. are preferred. Gas sparging or mixing can be used to aid the reaction.

In order that those skilled in the art will be better able to practice the present invention reference is made to the FIGURE, which shows an example of a continuous reactor system for producing aromatic carbonates. The symbol "V" indicates a valve and the symbol "P" indicates a pressure gauge.

The system includes a carbon monoxide gas inlet 10, an oxygen inlet 11, a manifold vent 12, and an inlet 13 for a gas, such as carbon dioxide. A reaction mixture can be fed into a low pressure reservoir 20, or a high pressure reservoir 21, which can be operated at a higher pressure than the reactor for the duration of the reaction. The system further includes a reservoir outlet 22 and a reservoir inlet 23. The gas feed pressure can be adjusted to a value greater than the desired reactor pressure with a pressure regulator 30. The gas can be purified in a scrubber 31 and then fed into a mass flow controller 32 to regulate flow rates. The reactor feed gas can be heated in a heat exchanger 33 having appropriate conduit prior to being introduced to a reaction vessel 40. The reaction vessel pressure can be controlled by a back pressure regulator 41. After passing through a condenser 25, the reactor gas effluent may be either sampled for further analysis at valve 42 or vented to the atmosphere at valve 50. The reactor liquid can be sampled at valve 43. An additional valve 44 can provide further system control, but is typically closed during the gas flow reaction.

In the practice of one embodiment of the invention, the carbonylation catalyst system and aromatic hydroxy compound are charged to the reactor system. The system is sealed. Carbon monoxide and oxygen are introduced into an appropriate reservoir until a preferred pressure (as previously defined) is achieved. Circulation of condenser water is initiated, and the temperature of the heat exchanger 33 (e.g., oil bath) can be raised to a desired operating temperature. A conduit 46 between heat exchanger 33 and reaction vessel 40 can be heated to maintain the desired operating temperature. The pressure in reaction vessel 40 can be controlled by the combination of reducing pressure regulator 30 and back pressure regulator 41. Upon reaching the desired reactor temperature, aliquots can be taken to monitor the reaction. Various preferred embodiments of the present method produce Pd TON of at least 1500. Even more preferred embodiments produce Pd TON of at least 2500.

EXAMPLES

The following examples are included to provide additional guidance to those skilled in the art in practicing the claimed invention. While some of the examples are illustrative of various embodiments of the claimed invention, others are comparative and are identified as such. The examples provided are merely representative of the work that contributes to the teaching of the present application. Accordingly, these examples are not intended to limit the invention, as defined in the appended claims, in any manner. Unless otherwise specified, all parts are by weight, and all equivalents are relative to palladium. Reaction products were verified by gas chromatography. For Examples 1–2 and Comparative Examples 1–2, reactions were carried out in a glass, batch reactor at 100° C. in an approximately 6–7% $O_2$ in CO atmosphere at an operating pressure of 109 atm. Reaction time was 3 hours for each run. Each reaction was run in replicate (3× or 4×) with the average of the replicate runs reported herein.

As discussed supra, the economics of aromatic carbonate production is dependent on the number of moles of aromatic carbonate produced per mole of Group VIII B metal utilized. In the following examples, the aromatic carbonate produced is diphenylcarbonate (DPC) and the Group VIII B metal utilized is palladium. For convenience, the number of moles of DPC produced per mole of palladium utilized is referred to as the palladium turnover number (Pd TON). Various preferred embodiments of the present method produce Pd TON of at least 1500. Even more preferred embodiments produce Pd TON of at least 2500.

Example 1

Diphenyl carbonate was produced by adding, at ambient conditions, 0.25 mM dichloro(1,4-bis(diphenylphosphino) butane)palladium(II) ["Pd(dppb)$Cl_2$"], 500 equivalents of chloride in various alkaline metal salt forms, 150 equivalents of hydroxide in the form of sodium hydroxide, 28 vol % tetraglyme, and various IOCC combinations in diverse amounts to a glass reaction vessel containing phenol. Lead was supplied as lead (II) oxide ("PbO"); titanium as titanium (IV) oxide acetylacetonate ("TiO(acac)$_2$"); copper as copper (II) acetylacetonate ("Cu(acac)$_2$"); cerium as cerium (III) acetylacetonate ("Ce(acac)$_3$"); and zirconium as zirconium (IV) butoxide ("Zr(OBu)$_4$"). The components were heated to 100° C. for 3 hours in an approximately 6–7% oxygen in carbon monoxide atmosphere. The following results were observed:

| Reaction No. | IOCC #1 | IOCC #1:Pd Equivalents | IOCC #2 | IOCC #2:Pd Equivalents | Halide | Pd TON |
|---|---|---|---|---|---|---|
| 1 | Cu(acac)$_2$ | 12 | TiO(acac)$_2$ | 5.6 | LiCl | 2033 |
| 2 | Cu(acac)$_2$ | 12 | TiO(acac)$_2$ | 5.6 | NaCl | 2292 |
| 3 | Cu(acac)$_2$ | 12 | TiO(acac)$_2$ | 5.6 | KCl | 1319 |
| 4 | Cu(acac)$_2$ | 12 | TiO(acac)$_2$ | 5.6 | CsCl | 935 |
| 5 | Cu(acac)$_2$ | 12 | Zr(OBu)$_4$ | 12 | LiCl | 1567 |
| 6 | Cu(acac)$_2$ | 12 | Zr(OBu)$_4$ | 12 | NaCl | 1533 |
| 7 | Cu(acac)$_2$ | 12 | Zr(OBu)$_4$ | 12 | KCl | 1716 |
| 8 | Cu(acac)$_2$ | 12 | Zr(OBu)$_4$ | 12 | CsCl | 1756 |
| 9 | PbO | 50 | Ce(acac)$_3$ | 5.6 | LiCl | 1399 |
| 10 | PbO | 50 | Ce(acac)$_3$ | 5.6 | NaCl | 885 |
| 11 | PbO | 50 | Ce(acac)$_3$ | 5.6 | KCl | 1208 |
| 12 | PbO | 50 | Ce(acac)$_3$ | 5.6 | CsCl | 588 |
| 13 | PbO | 50 | TiO(acac)$_2$ | 5.6 | LiCl | 1339 |
| 14 | PbO | 50 | TiO(acac)$_2$ | 5.6 | NaCl | 1298 |
| 15 | PbO | 50 | TiO(acac)$_2$ | 5.6 | KCl | 966 |
| 16 | PbO | 50 | TiO(acac)$_2$ | 5.6 | CsCl | 598 |

The various reaction conditions show that a Pd TON at least as high as 2292 can be obtained utilizing embodiments of the disclosed catalyst system. Based on the results of these experiments, it is evident that a catalyst system containing Pd, a base, an alkali chloride, a polyether, and numerous IOCC combinations can effectively catalyze the carbonylation reaction.

Example 2

The general procedure of Example 1 was repeated with 0.25 mM Pd(dppb)Cl$_2$, 500 equivalents of chloride in the form of potassium chloride, 150 equivalents of phenoxide in the form of sodium phenoxide, 28 vol % tetraglyme, and various IOCC combinations in various amounts. Manganese was supplied as manganese (III) acetylacetonate ("Mg(acac)$_3$"); iron as iron (III) acetylacetonate ("Fe(acac)$_3$"); nickel as nickel (II) acetylacetonate ("Ni(acac)$_2$"); and zinc as zinc (II) acetylacetonate ("Zn(acac)$_2$"). The following averaged results were observed:

| Reaction No. | IOCC #1 | IOCC #1:Pd Equivalents | IOCC #2 | IOCC #2:Pd Equivalents | Pd TON |
|---|---|---|---|---|---|
| 1 | PbO | 50 | — | — | 1420 |
| 2 | PbO | 50 | Ce(acac)$_3$ | 5.6 | 2043 |
| 3 | PbO | 24 | TiO(acac)$_2$ | 5.6 | 1164 |
| 4 | PbO | 50 | TiO(acac)$_2$ | 5.6 | 1684 |
| 5 | PbO | 50 | Mn(acac)$_3$ | 5.6 | 1741 |
| 6 | PbO | 50 | Zr(OBu)$_4$ | 12 | 1656 |
| 7 | Cu(acac)$_2$ | 24 | — | — | 608 |
| 8 | Cu(acac)$_2$ | 12 | TiO(acac)$_2$ | 5.6 | 402 |
| 9 | Cu(acac)$_2$ | 24 | Zr(OBu)$_4$ | 12 | 210 |

-continued

| Reaction No. | IOCC #1 | IOCC #1:Pd Equivalents | IOCC #2 | IOCC #2:Pd Equivalents | Pd TON |
|---|---|---|---|---|---|
| 10 | Cu(acac)$_2$ | 24 | Fe(acac)$_3$ | 5.6 | 970 |
| 11 | Cu(acac)$_2$ | 12 | Mn(acac)$_3$ | 10 | 352 |
| 12 | Cu(acac)$_2$ | 12 | Ni(acac)$_2$ | 10 | 414 |
| 13 | Ce(acac)$_3$ | 5.6 | Mn(acac)$_3$ | 10 | 635 |
| 14 | Ce(acac)$_3$ | 5.6 | Zn(acac)$_2$ | 50 | 184 |
| 15 | Ce(acac)$_3$ | 5.6 | Fe(acac)$_3$ | 10 | 389 |
| 16 | Zn(acac)$_2$ | 50 | TiO(acac)$_2$ | 5.6 | 396 |

The various reaction conditions show that a Pd TON at least as high as 2043 can be obtained utilizing embodiments of the disclosed catalyst system.

Example 3

A batch-batch reactor system was charged at ambient conditions with a phenol:cosolvent mixture containing diverse amounts of various catalyst components. Molecular sieves (1.6 mm diameter pellets, 3 Å, 30 grams) were placed in a perforated polytetrafluoroethylene basket mounted to the reactor's stir shaft. The reactor vessel was sealed and pressurized to 109 atm. with a 9% oxygen in CO atmosphere. The reactor was heated to 100° C. over 10 minutes and stirred at 1600 rpm while maintaining 100° C. during a 3.5 hour reaction run. Liquid sampling of the reactor contents was performed every 30 minutes via a sample dip tube located in the reactor. Sample aliquots were analyzed by HPLC for DPC. The data listed below correspond to the point of maximum yield for each reaction run in the presence of 400 equivalents of NaOH:

| Run No. | [Pd(acac)$_2$] mM | IOCC #1 | IOCC #1:Pd Equivalents | IOCC #2 | IOCC #2:Pd Equivalents | Halide | Co-solvent | Pd TON |
|---|---|---|---|---|---|---|---|---|
| 1 | 0.25 | PbO | 50 | Ce(acac)$_3$ | 9 | KCl | Tetraglyme | 1788 |
| 2 | 0.25 | PbO | 50 | Ce(acac)$_3$ | 9 | NaCl | Tetraglyme | 686 |
| 3 | 0.25 | PbO | 50 | Ce(acac)$_3$ | 9 | KCl | CH$_3$CN | 1425 |
| 4 | 0.25 | PbO | 50 | TiO(acac)$_2$ | 6 | KCl | Tetraglyme | 933 |
| 5 | 0.15 | Cu(acac)$_2$ | 5 | TiO(acac)$_2$ | 6 | NaCl | Tetraglyme | 5925 |
| 6 | 0.15 | Cu(acac)$_2$ | 5 | TiO(acac)$_2$ | 6 | NaCl | CH$_3$CN | 1121 |
| 7 | 0.15 | Cu(acac)$_2$ | 5 | TiO(acac)$_2$ | 6 | KCl | Tetraglyme | 4622 |

The various reaction conditions show that a Pd TON at least as high as 5925 can be obtained utilizing embodiments of the disclosed catalyst system.

Comparative Example A

To show the comparative effectiveness of the previously detailed catalyst systems, replicate runs were conducted using the general procedure of Examples 1–2 with 0.25 mM Pd(dppb)Cl$_2$, 500 equivalents of chloride in the form of tetrabutylammonium chloride ("TBACl"), 150 equivalents of NaOH, and where applicable 28 vol % tetraglyme. The results are shown below:

| Reaction No. | IOCC #1 | IOCC #1:Pd Equivalents | IOCC #2 | IOCC #2:Pd Equivalents | Tetraglyme | Pd TON |
| --- | --- | --- | --- | --- | --- | --- |
| 1 | Cu(acac)$_2$ | 12 | Zr(OBu)$_4$ | 12 | No | 1937 |
| 2 | Cu(acac)$_2$ | 12 | Zr(OBu)$_4$ | 12 | Yes | 1908 |
| 3 | PbO | 50 | Ce(acac)$_3$ | 5.6 | No | 1846 |
| 4 | PbO | 50 | Ce(acac)$_3$ | 5.6 | Yes | 1161 |
| 5 | PbO | 50 | TiO(acac)$_2$ | 5.6 | No | 1912 |
| 6 | PbO | 50 | TiO(acac)$_2$ | 5.6 | Yes | 1148 |

When compared with Example 1, these results illustrate that the performance of the present system approximates that of systems containing onium chloride compounds. More importantly, the comparative costs of alkaline metal chlorides and onium chlorides underscore the substantial economic advantages of the present system. It is also noted that the performance of these onium chloride systems decreased with the addition of tetraglyme at the conditions used.

Comparative Example B

Replicate runs were conducted using the general procedure of Example 2. The runs were carried out in the absence of a base with the following results:

| Reaction No. | IOCC #1 | IOCC #1:Pd Equivalents | IOCC #2 | IOCC #2:Pd Equivalents | Pd TON |
| --- | --- | --- | --- | --- | --- |
| 1 | PbO | 50 | — | — | 1017 |
| 2 | PbO | 50 | Ce(acac)$_3$ | 5.6 | 1118 |
| 3 | PbO | 24 | TiO(acac)$_2$ | 5.6 | 253 |
| 4 | PbO | 50 | TiO(acac)$_2$ | 5.6 | 916 |
| 5 | PbO | 50 | Mn(acac)$_3$ | 5.6 | 1055 |
| 6 | PbO | 50 | Zr(OBu)$_4$ | 12 | 733 |
| 7 | Cu(acac)$_2$ | 24 | — | — | 31 |
| 8 | Cu(acac)$_2$ | 12 | TiO(acac)$_2$ | 5.6 | 39 |
| 9 | Cu(acac)$_2$ | 24 | Zr(OBu)$_4$ | 12 | 146 |
| 10 | Cu(acac)$_2$ | 24 | Fe(acac)$_3$ | 5.6 | 33 |
| 11 | Cu(acac)$_2$ | 12 | Mn(acac)$_3$ | 10 | 26 |
| 12 | Cu(acac)$_2$ | 12 | Ni(acac)$_2$ | 10 | 32 |
| 13 | Ce(acac)$_3$ | 5.6 | Mn(acac)$_3$ | 10 | 99 |
| 14 | Ce(acac)$_3$ | 5.6 | Zn(acac)$_2$ | 50 | 143 |
| 15 | Ce(acac)$_3$ | 5.6 | Fe(acac)$_3$ | 10 | 6 |
| 16 | Zn(acac)$_2$ | 50 | TiO(acac)$_2$ | 5.6 | 174 |

These results illustrate that the catalyst systems of Example 2 perform substantially better than the systems without base.

Comparative Example C

The general procedure of Example 3 was repeated with selected combinations of tetraethylammonium chloride ("TEACl"), tetramethylammonium chloride (TMACl), and tetraglyme to show the comparative effectiveness of the present catalyst system. The following results were observed:

| Run No. | [Pd(acac)$_2$] mM | IOCC #1 | IOCC #1:Pd Equivalents | IOCC #2 | IOCC #2:Pd Equivalents | Halide | Tetraglyme | Pd TON |
| --- | --- | --- | --- | --- | --- | --- | --- | --- |
| 1 | 0.25 | PbO | 50 | Ce(acac)$_3$ | 9 | TEACl | No | 2106 |
| 2 | 0.25 | PbO | 50 | Ce(acac)$_3$ | 9 | TMACl | Yes | 1218 |

The following illustrative chloride costs were taken from the *Chemical Marketing Reporter*, February 1999:

| Chloride Source | $/pound | $/mole Cl |
| --- | --- | --- |
| TMACl | 3.65 | 0.88 |
| TEACl | 2.75 | 1.00 |
| NaCl | 0.29 | 0.04 |
| KCl | 0.54 | 0.09 |

When compared with the results in Example 3 and assuming that all chloride cocatalyst has to be replenished with virgin chloride salts (i.e., no chloride recycle), it is evident that the present system can exhibit substantial economic advantages over systems employing more expensive onium chlorides.

It will be understood that each of the elements described above, or two or more together, may also find utility in applications differing from the types described herein. While the invention has been illustrated and described as embodied in a method and catalyst system for producing aromatic carbonates, it is not intended to be limited to the details shown, since various modifications and substitutions can be made without departing in any way from the spirit of the present invention. For example, additional effective IOCC compounds can be added to the reaction. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A carbonylation catalyst system, comprising catalytic amounts of the following components:

a Group VIII B metal source;

an alkaline metal chloride;

a polyether; and a base;

said catalytic amounts being amounts capable of increasing the yield of aromatic carbonate in the reaction of an aromatic hydroxy compound, carbon monoxide and oxygen or increasing selectivity of said reaction toward aromatic carbonate.

2. The carbonylation catalyst system of claim 1, wherein the polyether is tetraethylene glycol dimethyl ether.

3. The carbonylation catalyst system of claim 1, further comprising catalytic amounts of at least one inorganic cocatalyst comprising a non-Group VIIIB metal source.

4. The carbonylation catalyst system of claim 3, wherein the non-Group VIIIB metal source includes lead.

5. The carbonylation catalyst system of claim 1, further comprising a combination of at least two inorganic cocatalysts, each comprising a non-Group VIIIB metal source.

6. The carbonylation catalyst system of claim 5, wherein the combination of inorganic cocatalysts includes a copper source and a zirconium source.

7. The carbonylation catalyst system of claim 5, wherein the combination of inorganic cocatalysts includes a copper source and a titanium source.

8. The carbonylation catalyst system of claim 5, wherein the combination of inorganic cocatalysts includes a lead source and a cerium source.

9. The carbonylation catalyst system of claim 5, wherein the combination of inorganic cocatalysts includes a lead source and a titanium source.

10. The carbonylation catalyst system of claim 1, wherein the Group VIIIB metal source is a palladium source.

11. The carbonylation catalyst system of claim 10, wherein the palladium source is a non-supported Pd(II) salt or complex.

12. The carbonylation catalyst system of claim 1, wherein the base is sodium hydroxide.

13. The carbonylation catalyst system of claim 1, wherein the alkaline metal chloride is an alkali metal chloride or an alkaline earth metal chloride.

* * * * *